United States Patent [19]

Morgan

[11] Patent Number: 4,657,910
[45] Date of Patent: Apr. 14, 1987

[54] TREATMENT OF CEREBROVASCULAR DISORDERS AND/OR DISORDERS ASSOCIATED WITH CEREBRAL SENILITY

[75] Inventor: Brian Morgan, Reigate, England

[73] Assignee: Beecham-Wuelfing GmbH & Co. KG, Fed. Rep. of Germany

[21] Appl. No.: 837,014

[22] Filed: Mar. 6, 1986

Related U.S. Application Data

[63] Continuation of Ser. No. 756,015, Jul. 17, 1985, abandoned.

[30] Foreign Application Priority Data

Jul. 19, 1984 [GB] United Kingdom ............... 8418430

[51] Int. Cl.$^4$ ............................................. A61K 31/52
[52] U.S. Cl. ................................................. 514/263
[58] Field of Search ..................................... 514/263

[56] References Cited

U.S. PATENT DOCUMENTS

| | | | |
|---|---|---|---|
| 4,225,607 | 9/1980 | Goring et al. | 544/267 |
| 4,242,345 | 12/1980 | Brenner | 544/267 |
| 4,372,959 | 2/1983 | Goring | 544/267 |
| 4,451,449 | 5/1984 | Goring | 544/267 |
| 4,454,138 | 6/1984 | Goring | 544/267 |

FOREIGN PATENT DOCUMENTS 0018135 9/1983 European Pat. Off. .

OTHER PUBLICATIONS

Giurgea et al., Prog. Neuro-Psychopharmac., vol. 1, 235-247 (1977).
British Medical Journal, No. 6189, 511-512 (Sep. 1, 1979).
Izquierdo et al., Acta. Physiol. Latino-Americana, 3, 207-209 (1981).
AMA Drug Evaluations, Fifth Edition, 281-285, 674-685 (1983).
Lowe, British Medical Journal, 286, 1262-1264 (Apr. 16, 1983).
Sakai et al., Jap. J. Pharmacol., 33, 236P-187 (1983).
Bentue-Ferrer et al., Experimental Aging Research, 11, 137-141 (1985).
Gamzu, Ann. N.Y. Acad. Sci., 444, 370-393 (1985).
Scrip, No. 1065/66, 26-27, (Jan. 8, 1986).

*Primary Examiner*—Stanley J. Friedman
*Attorney, Agent, or Firm*—Jacobs & Jacobs

[57] ABSTRACT

A method for the treatment and/or prophylaxis of cerebrovascular disorders and/or disorders associated with cerebral senility in mammals, such as humans, which comprises administering to the mammal in need of such treatment and/or prophylaxis an effective and/or prophylactic amount of a compound of formula (I):

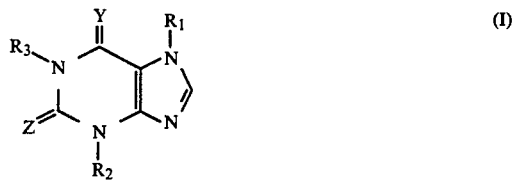

wherein
(i) $R_1$ is a group $-X-CO-CH_3$ where X is a hydrocarbon radical having up to 4 carbon atoms which may be substituted by a methyl group,
$R_2$ and $R_3$, which may be the same or different, each represents a straight-chain or branched-chain alkyl radical of 2 to 6 carbon atoms, or a cyclohexyl, alkoxyalkyl or hydroxyalkyl radical, and
Y and Z each represent oxygen;
(ii) $R_1$ is a group $-CH_2(OR_4)(OR_5)CH_3$ wherein $R_4$ is an alkyl radical of 1 to 4 carbon atoms and $R_5$ is an alkyl radical of 1 to 4 carbon atoms or $R_4$ is linked to $R_5$ so that the $OR_4$ and $OR_5$ moieties and the carbon atoms to which they are attached form a 1,3-dioxacylohexa-2,2-diyl,1,3-dioxacyclopenta-2,2-diyl or 1,3-dioxacyclohepta-2,2-diyl diradical,
$R_2$ and $R_3$ are the same or different and are each an alkyl radical of 1 to 4 carbon atoms, and
Y and Z each represent oxygen; (iii) $R_1$ is a group $-CH_2COCH_3$,
$R_2$ is an alkyl radical of 1 to 6 carbon atoms,
$R_3$ is an alkyl radical of 1 to 6 carbon atoms,
Z is sulphur and Y is oxygen or sulphur;
(iv) $R_1$ is a group $-(CH_2)_nCOCH_3$ where n is 1 or 2, one of $R_2$ and $R_3$ is an alkyl radical of 1 to 6 carbon atoms and the other is an alkyl radical of 2 to 6 carbon atoms,
Z is oxygen and Y is sulphur; or
(v) $R_1$ is a group $-CH_2COCH_3$,
$R_2$ is an alkyl radical of 1 to 4 carbon atoms,
$R_3$ is a group $CH_3CO(CH_2)_4-$, and
Y and Z each represent oxygen.

8 Claims, No Drawings

TREATMENT OF CEREBROVASCULAR DISORDERS AND/OR DISORDERS ASSOCIATED WITH CEREBRAL SENILITY

CROSS-REFERENCE

This is a continuation of Ser. No. 756,015 filed July 17, 1985 now abandoned.

The present invention relates to a method for the treatment and/or prophylaxis of cerebrovascular disorders and/or disorders associated with cerebral senility.

British patent specification No. 1441562 discloses compounds of formula (A):

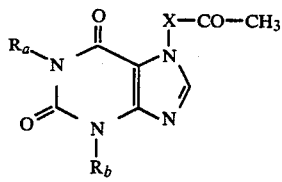

wherein $R_a$ and $R_b$ which may be the same or different, each represents a straight-chain or branched-chain alkylradical of 2 to 6 carbon atoms, or a cyclohexyl, alkoxyalkyl or hydroxyalkyl radical, and X represents a hydrocarbon radical having up to 4 carbon atoms which may be substituted by a methyl group. The compounds of the formula (A) are described as effective in increasing the blood flow through skeletal muscles while at the same time showing low toxicity.

EP-0005015-A discloses that the compound of formula (A) wherein $R_a$ and $R_b$ are both n-butyl groups and X is a $CH_2$ group, i.e. 1,3-di-n-butyl-7-oxopropyl xanthine, is effective in increasing oxygen tension and contractility in ischaemic skeletal muscle and is therefore of potential use in the treatment of peripheral vascular disease.

EP-0018135-A discloses compounds of the formula (B):

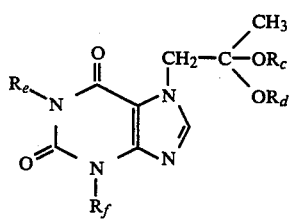

wherein
$R_c$ is a lower alkyl group and $R_d$ is a lower alkyl group; or
$R_c$ is linked to $R_d$ so that the $OR_c$ and $OR_d$ moieties and the carbon atom to which they are attached form a 1,3-dioxacyclohexa-2,2-diyl, 1,3-dioxacyclopenta-2,2-diyl or 1,3-dioxacyclohepta-2,2-diyl diradical; and
$R_e$ and $R_f$ are the same or different and are each a lower alkyl group; in which the term "lower" means containing 1 to 4 carbon atoms.

The compounds of the formula (B) are described for use in the treatment of vascular disorders such as intermittent claudication.

EP-0018136-A discloses compounds of formula (C)

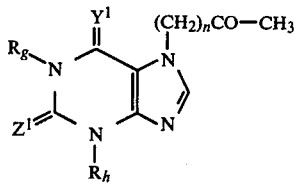

wherein
$Z^1$ is sulphur and $Y^1$ is oxygen or sulphur;
$R_g$ is an alkyl group of up to 6 carbon atoms;
$R_h$ is an alkyl group of up to 6 carbon atoms; and
n is 1; or
$Z^1$ is oxygen and $Y^1$ is sulphur;
one of $R_g$ and $R_h$ is an alkyl group of up to 6 carbon atoms and the other is an alkyl group of 2 to b 6 carbon atoms; and
n is 1 or 2.

Compounds of formula (C) are disclosed as effective in improving the metabolic status of ischaemic skeletal muscle by increasing oxygen tension and/or contractility in the tissue, and are thus of potential use as agents for the treatment of peripheral vascular disease such as intermittent claudication.

EP-0042706-A discloses compounds of formula (D):

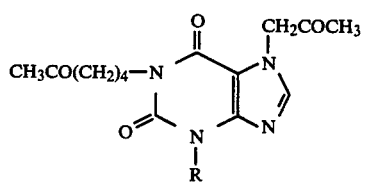

wherein $R_i$ is an alkyl group of 1 to 4 carbon atoms. The compounds of formula (D) are described as active in increasing oxygen tension in ischaemic skeletal muscle and as useful in the treatment of peripheral vascular disorders such as intermittent claudication.

It has now been discovered that the compounds of formula (A), (B), (C) and (D) also have a protective effect against the consequences of cerebral metabolic inhibition and/or enhance cognition in animals. The compounds are therefore of potential use in the treatment of cerebrovascular disorders and disorders associated with cerebral senility in mammals including humans.

Accordingly, the present invention provides a method for the treatment and/or prophylaxis of cerebrovascular disorders and/or disorders associated with cerebral senility in mammals, such as humans, which comprises administering to the mammal in need of such treatment and/or prophylaxis an effective and/or prophylactic amount of a compound of formula (I):

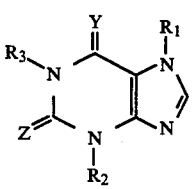

wherein (i) $R_1$ is a group $-X-CO-CH_3$ where X is a hydrocarbon radical having up to 4 carbon atoms which may be substituted by a methyl group, $R_2$ and $R_3$, which may be the same or different, each represents a straight-chain or branched-chain alkyl radical of 2 to 6 carbon atoms, or a cyclohexyl, alkoxyalkyl or hydroxyalkyl radical, and Y and Z each represent oxygen;

(ii) $R_1$ is a group $-CH_2(OR_4)(OR_5)CH_3$ wherein $R_4$ is an alkyl radical of 1 to 4 carbon atoms and $R_5$ is an alkyl radical of 1 to 4 carbon atoms or $R_4$ is linked to $R_5$ so that the $OR_4$ and $OR_5$ moieties and the carbon atoms to which they are attached form a 1,3-dioxacylohexa-2,2-diyl, 1,3-dioxacyclopenta-2,2-diyl or 1,3-dioxacyclohepta-2,2-diyl diradical, $R_2$ and $R_3$ are the same or different and are each an alkyl radical of 1 to 4 carbon atoms, and Y and Z each represent oxygen;

(iii) $R_1$ is a group $-CH_2COCH_3$,
$R_2$ is an alkyl radical of 1 to 6 carbon atoms,
$R_3$ is an alkyl radical of 1 to 6 carbon atoms,
Z is sulphur and Y is oxygen or sulphur;

(iv) $R_1$ is a group $-(CH_2)_nCOCH_3$ where n is 1 or 2, one of $R_2$ and $R_3$ is an alkyl radical of 1 to 6 carbon atoms and the other is an alkyl radical of 2 to 6 carbon atoms, Z is oxygen and Y is sulphur; or (v) $R_1$ is a group $-CH_2COCH_3$,
$R_2$ is an alkyl radical of 1 to 4 carbon atoms,
$R_3$ is a group $CH_3CO(CH_2)_4-$, and
Y and Z each represent oxygen.

The administration to the mammal may be by way of oral administration or parenteral administration.

An amount effective to treat the disorders hereinbefore described depends on the usual factors such as the nature and severity of the disorders being treated and the weight of the mammal. However, a unit dose will normally contain 1 to 100 mg for example 2 to 50 mg, of the compound of the invention. Unit doses will normally be administered once or more than once a day, for example 2, 3, 4, 5 or 6 times a day, more usually 2 to 4 times a day, such that the total daily dose is normally in the range, for a 70 kg adult of 0.1 to 250 mg, for example 50 to 150 mg, that is in the range of approximately 0.002 to 3.5 mg/kg/day, more usually 1 to 3 mg/kg/day, for example 0.7 to 2 mg/kg/day.

It is greatly preferred that the compound of formula (I) is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as anti-hypertensive agents and diuretics.

As is common practice, the compositions will usually be accompanied by written or printed directions for use in the medical treatment concerned.

The present invention also provides a compound of formula (I) for use in the treatment and/or prophylaxis of cerebrovascular disorders and/or disorders associated with cerebral senility. Such treatment and/or prophylaxis may be carried out as hereinbefore described.

Suitable values for the variables in formula (I) are as follows:

(i) $R_1$ is $-X-CO-CH_3$ where X is $-CH_2-$, $-(CH_2)_2-$, $-(CH_2)_3-$, $-(CH_2)_4-$, $-CH(CH_3)-$ or $-CH(CH_3)CH_2-$.

$R_2$ and $R_3$ are iso-propyl or n-butyl.

Y and Z are oxygen.

(ii) $R_1$ is —$CH_2(OR_4)(OR_5)CH_3$ where $R_4$ and $R_5$ are methyl or ethyl or $OR_4$ and $OR_5$ together with the carbon atoms to which they are attached represent 1,3-dioxacyclopenta-2,2-diyl.
$R_2$ and $R_3$ are ethyl or n-butyl.
Y and Z are oxygen.
(III) $R_1$ is —$CH_2COCH_3$.
$R_2$ and $R_3$ are ethyl or n-butyl, preferably n-butyl.
Y is oxygen or sulphur and Z is sulphur.
(iv) $R_1$ is —$CH_2COCH_3$.
$R_2$ is butyl and $R_3$ is ethyl.
Y is sulphur and Z is oxygen.
(v) $R_1$ is —$CH_2COCH_3$.
$R_2$ is n-butyl.
$R_3$ is $CH_3CO(CH_2)_4$—.
Y and Z are oxygen.

A preferred sub-group of the compounds of formula (I) comprises compounds in which at least one of $R_2$ and $R_3$ is an n-butyl group. Preferably both of $R_2$ and $R_3$ are n-butyl.

Another preferred sub-group of the compounds of formula (I) comprises compounds in which $R_1$ is a group —X—CO—$CH_3$ where X is a hydrocarbon radical having up to 4 carbon atoms which may be substituted by a methyl group, $R_2$ and $R_3$, which may be the same or different, each represents a straight-chain or branched-chain alkyl radical of 2 to 6 carbon atoms, or a cyclohexyl, alkoxyalkyl or hydroxyalkyl radical, and Y and Z each represent oxygen.

Suitable compounds of formula (I) are as follows:
1,3-Di-n-butyl-7-(2-oxopropyl)xanthine,
1,3-Di-n-butyl-7-(3-oxobutyl)xanthine,
1,3-Diethylxanthinyl-7-ylpropan-2-one diethyl ketal,
1,3-Di-n-butyl-7-(2-oxopropyl)-2-thioxanthine,
-(5-oxohexyl)-3-n-butyl-7-(2-oxopropyl)xanthine.

Other suitable compounds are those exemplified in GB1441562, EP-0018135-A, EP-0018136-A and EP-0042706-A.

A preferred compound of formula (I) is 1,3-Di-n-butyl-7-(2-oxopropyl)xanthine.

The present invention further provides a pharmaceutical composition for use in the treatment and/or prophylaxis of cerebrovascular disorders and/or disorders associated with cerebral senility, which comprises a compound of formula (I) and a pharmaceutically acceptable carrier.

In a further aspect the invention provides the use of a compound of formula (I) for the manufacture of a medicament for the treatment or prophylaxis of cerebrovascular disorders and/or disorders associated with cerebral senility.

Such compositions may be prepared in the manner as hereinbefore described.

The following pharmacological data illustrate the activity of compounds of formula (I) in tests which are indicative of compounds of potential use in the treatment of cerebrovascular disorders and disorders associated with cerebral senility in mammals.

PHARMACOLOGICAL DATA

1. Triethyltin-induced Cerebral Oedema in the Rat

The cerebral oedema is induced by oral administrations repeated for 5 consecutive days—one administration per day—of triethyltin chloride at a dose of 2 mg/kg. The test compound is also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used:
1 control group
1 group intoxicated with triethyltin
1 group intoxicated with triethyltin and treated with the studied compound.

The rats are sacrificed on the evening of the fifth day; the brain is removed, weighed fresh and after desiccation to constant weight and the water content of each brain is calculated:

[$H_2O$] = fresh weight − dry weight.

The following are then calculated:
the mean water content (M±Sm%) of each group;
the protection index P due to the administered compound:

$$P\% = 1 - \frac{[H_2O] \text{ treated group} - [H_2O] \text{ control group}}{[H_2O] \text{ triethyltin group} - [H_2O] \text{ control group}} \times 100$$

The significance is evaluated:
by the Student t-test; *P<0.001, P<0.01.
or by the Darmois t'-test: Δ=significant.
The results are shown in Table I.

TABLE I

Triethyltin-induced cerebral oedema
% protection at a dose administered (mg · kg$^{-1}$ p.o.)

| Test Compound (No.) | 2 × 1 | 2 × 5 | 2 × 10 | 2 × 12.5 | 2 × 50 | 2 × 100 |
|---|---|---|---|---|---|---|
| 1,3-Di-n-butyl-7-(2-oxopropyl)xanthine (1) | 39*** | 80Δ | ±(100***) (88***) | — | — | — |
| 1,3-Di-n-butyl-7-(3-oxobutyl)xanthine (2) | — | — | — | — | — | 24* |
| 1,3-Diethyl-xanthinyl-7-ylpropan-2-one diethyl ketal (3) | — | — | — | — | 47** | — |
| 1,3-Di-n-butyl-7-(2-oxopropyl)-2-thioxanthine (4) | — | — | — | 36** | — | — |
| 1-(5-Oxohexyl)-3-n-butyl-7- | — | — | — | — | 71** | — |

TABLE I-continued

| | Triethyltin-induced cerebral oedema % protection at a dose administered (mg · kg$^{-1}$ p.o.) | | | | | |
|---|---|---|---|---|---|---|
| Test Compound (No.) | 2 × 1 | 2 × 5 | 2 × 10 | 2 × 12.5 | 2 × 50 | 2 × 100 |
| (2-oxopropyl)xanthine (5) | | | | | | |

± results obtained from two series of experiments.

2. Passive Avoidance in the Mouse

Male CD1 mice (Charles River, approximately 24–28 g) housed 5 to a cage, were trained on a one-trial step-through passive avoidance task (n=30 per group). This task is extensively used to test the effects of drugs upon learning and memory (Bammer 1982). The apparatus consisted of 2 compartments, a 'start'-box constructed of transparent perspex and a 'dark'-box of black perspex connected by a small opening in their common wall which could be closed by means of a sliding door. The 'dark'-box was traversed by 2 photocell beams, one, across the doorway between the 'dark'-and 'start'-boxes, and the second located some 10 cms into the body of the box.

Training commenced with the subject being placed in the 'start'-box for 30 seconds. At the end of this time the door was raised allowing access to the 'dark'-box. The step-through latency on training was defined as the interval between the first interruption of the first and second photocell beams in seconds. Five seconds after the interruption of the second beam a scrambled foot-shock (0.2 mA for 1 second) was delivered to the grid floor of the 'dark'-box. Animals were allowed to escape back to the 'start'-box from which they were removed. Subjects not escaping spontaneously from the 'dark'-box were removed by hand.

Upon removal from the apparatus subjects received subcutaneous injections of 0.5 mg/kg of Compound (1) in a saline containing (by volume) 10% DMSO, or the carrier alone and returned to their home cages. The injection volume was 0.1 ml/10 g body weight.

Recall testing of the previously learned association between the 'dark'-box and footshock was carried out 24 hours later using a procedure which was similar to that used for training, except insofar as footshock was not employed. Step-through latencies were timed up to a criterion. Animals failing to step-through within 600 seconds of breaking the first photocell beam were removed from the apparatus and assigned latencies of 600 seconds for the purposes of analysis. A similar procedure was adopted towards animals failing to interrupt the first beam within 600 seconds of the door being raised.

Both training and recall latencies were analysed by means of Mann-Whitney U-tests with the results expressed as Z scores. All tests were 2-tailed. On initial training the step-through mean latency of the control group was 9.1 sec. (SD=5.7) while that of the treatment group was 8.0 (SD=7.8)). The difference between groups was not significant (Z=1.32, ns). On recall testing the mean latency of the controls was 135.9 (SD=161.9) while that of the group treated with Compound (1) was 245.1 (SD=215.4). This difference was significant (Z=2.18, p<0.05) and was interpreted as being consistent with the hypothesis that treatment with Compound (1) immediately after training improves the retention of previously acquired information.

A second study was carried out in the same apparatus, again using male CD1 mice (n=20 per group). Mice were trained as before, but this time one group was orally treated with Compound (1) (10 mg/kg in 1% methylcellulose) and the other with 1% methylcellulose alone. Dosing in both cases was carried out 15 minutes prior to recall testing. Again the injection volume was 0.1 ml per 10 g body weight and there were no significant differences between groups with respect to training latency (mean control group=11.6 sec. SD=14.2, mean Compound (1) group=12.9, SD=11.7, Z=1.24, ns). However, animals treated with Compound (1) had longer recall latencies (mean=476.2. SD=182.2) than animals receiving vehicle alone (mean=298.8, SD=228.3). This difference was significant (Z=2.45, p<0.05) and suggests that Compound (1) may facilitate the retrieval of previously acquired information.

Reference: Bammer, G. Pharmacological investigations of neurotransmitter involvement in passive avoidance responding: A review and some new results. Neuroscience and Biobehavioural Reviews, 6, 247–296, 1982.

TOXICITY

No toxic effects were observed in the above tests.

I claim:

1. A method for the treatment of cerebrovascular disorders and/or disorders associated with cerebral senility in mammals, which comprises administering to the mammal in need of such treatment an effective amount of a compound of formula (I):

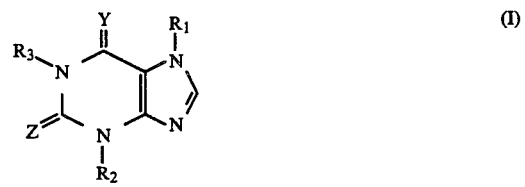

wherein
(i) $R_1$ is a group —X—CO—CH$_3$ where X is a hydrocarbon radical having up to 4 carbon atoms which may be substituted by a methyl group,
$R_2$ and $R_3$, which may be the same or different, each represents a straight-chain or branched-chain alkyl radical of 2 to 6 carbon atoms, or a cyclohexyl, alkoxyalkyl or hydroxyalkyl radical, and
Y and Z each represent oxygen;
(ii) $R_1$ is a group —CH$_2$(OR$_4$)(OR$_5$)CH$_3$ wherein $R_4$ is an alkyl radical of 1 to 4 carbon atoms and $R_5$ is an alkyl radical of 1 to 4 carbon atoms or $R_4$ is linked to $R_5$ so that the OR$_4$ and OR$_5$ moieties and the carbon atoms to which they are attached form a 1,3-dioxacylohexa-2,2-diyl,1,3-dioxacyclopenta-2,2-diyl or 1,3-dioxacyclohepta-2,2-diyl diradical, $R_2$ and $R_3$ are the same or different and are each an alkyl radical of 1 to 4 carbon atoms, and
Y and Z each represent oxygen;

(iii) $R_1$ is a group —$CH_2COCH_3$,
  $R_2$ is an alkyl radical of 1 to 6 carbon atoms,
  $R_3$ is an alkyl radical of 1 to 6 carbon atoms,
  Z is sulphur and Y is oxygen or sulphur;
(iv) $R_1$ is a group —$(CH_2)_nCOCH_3$ where n is 1 or 2, one of $R_2$ and $R_3$ is an alkyl radical of 1 to 6 carbon atoms and the other is an alkyl radical of 2 to 6 carbon atoms,
  Z is oxygen and Y is sulphur; or
(v) $R_1$ is a group —$CH_2COCH_3$,
  $R_2$ is an alkyl radical of 1 to 4 carbon atoms,
  $R_3$ is a group $CH_3CO(CH_2)_4$—, and
  Y and Z each represent oxygen.

2. A method according to claim 1, wherein at least one of $R_2$ and $R_3$ is an n-butyl group.

3. A method according to claim 1, wherein $R_1$ is a group —X—CO—$CH_3$ where X is a hydrocarbon radical having up to 4 carbon atoms which may be substituted by a methyl group, $R_2$ and $R_3$, which may be the same or different, each represents a straight-chain or branched-chain alkyl radical of 2 to 6 carbon atoms, or a cyclohexyl, alkoxyalkyl or hydroxyalkyl radical, and Y and Z each represent oxygen.

4. A method according to claim 3, wherein the compound of formula (I) is 1,3-di-n-butyl-7-(2-oxopropyl)xanthine.

5. A method according to claim 3, wherein the compound of formula (I) is 1,3-di-n-butyl-7-(3-oxobutyl)xanthine.

6. A method according to claim 1, wherein the compound of formula (I) is 1,3-diethylxanthinyl-7-ylpropan-2-one diethyl ketal.

7. A method according to claim 2, wherein the compound of formula (I) is 1,3-di-n-butyl-7-(2-oxopropyl)-2-thioxanthine.

8. A method according to claim 2, wherein the compound of formula (I) is 1-(5-oxohexyl)-3-n-butyl-7-(2-oxopropyl)xanthine.

* * * * *

UNITED STATES PATENT AND TRADEMARK OFFICE
CERTIFICATE OF CORRECTION

PATENT NO. : 4,657,910

DATED : April 14, 1987

INVENTOR(S) : Brian Morgan

It is certified that error appears in the above-identified patent and that said Letters Patent are hereby corrected as shown below:

Col. 5, line 35, insert --1-- before "-(5-oxohexyl)".

Signed and Sealed this

Twenty-third Day of February, 1988

Attest:

DONALD J. QUIGG

*Attesting Officer*    *Commissioner of Patents and Trademarks*